(12) United States Patent
Gill (10) Patent No.: US 9,278,012 B2
(45) Date of Patent: Mar. 8, 2016

(54) PROSTHESIS OR AN ORTHOSIS AND A METHOD FOR CONTROLLING A PROSTHESIS OR AN ORTHOSIS

(75) Inventor: Hugh Gill, Livingston (GB)

(73) Assignee: Touch Bionics Limited, Livingston (GB)

( * ) Notice: Subject to any disclaimer, the term of this patent is extended or adjusted under 35 U.S.C. 154(b) by 23 days.

(21) Appl. No.: 14/236,132

(22) PCT Filed: Aug. 29, 2012

(86) PCT No.: PCT/GB2012/052111
§ 371 (c)(1),
(2), (4) Date: Apr. 29, 2014

(87) PCT Pub. No.: WO2013/038143
PCT Pub. Date: Mar. 21, 2013

(65) Prior Publication Data
US 2014/0288665 A1    Sep. 25, 2014

(30) Foreign Application Priority Data

Sep. 16, 2011    (GB) .................................. 1116060.3

(51) Int. Cl.
*A61F 2/58* (2006.01)
*A61H 1/02* (2006.01)
*A61F 2/68* (2006.01)
(Continued)

(52) U.S. Cl.
CPC .................. *A61F 2/583* (2013.01); *A61F 2/586* (2013.01); *A61F 2/68* (2013.01); *A61F 5/013* (2013.01); *A61H 1/0288* (2013.01); *A61F 2002/701* (2013.01); *A61F 2002/704* (2013.01); *A61F 2002/7615* (2013.01);
(Continued)

(58) Field of Classification Search
CPC ..... B25J 11/004; B25J 15/0004; B25J 15/086
See application file for complete search history.

(56) References Cited

U.S. PATENT DOCUMENTS

| 2,669,727 A | 2/1954 | Opuszenski |
| 3,866,246 A | 2/1975 | Seamone et al. |

(Continued)

FOREIGN PATENT DOCUMENTS

| CN | 1803413 | 7/2006 |
| EP | 0145504 | 6/1985 |

(Continued)

OTHER PUBLICATIONS

Stix, "Phantom Touch: Imbuing a Prosthesis with Manual Dexterity" (Scientific American: Oct. 1998, pp. 41 and 44).*

(Continued)

*Primary Examiner* — David H Willse
(74) *Attorney, Agent, or Firm* — K&L Gates LLP (57) ABSTRACT

A prosthesis or an orthosis and a method of controlling movable components of the same. The prosthesis or orthosis comprises a plurality of movable components, each component being movable by a respective motor and a control device operative to determine when movement of at least a first component is arrested when the at least first component bears against a surface, and to move one or more further components with respective one or more further motors so that each subsequent component is moved upon determination that the movement of the preceding component is arrested when the preceding component bears against a surface.

46 Claims, 3 Drawing Sheets (51) Int. Cl.
 A61F 5/01 (2006.01)
 B25J 15/08 (2006.01)
 B25J 15/00 (2006.01)
 A61F 2/70 (2006.01)
 A61F 2/76 (2006.01)

(52) U.S. Cl.
 CPC ..... *A61F 2005/0155* (2013.01); *B25J 15/0004* (2013.01); *B25J 15/086* (2013.01)

(56) References Cited

U.S. PATENT DOCUMENTS

| | | | |
|---|---|---|---|
| 4,558,704 | A | 12/1985 | Petrofsky |
| 4,623,354 | A | 11/1986 | Childress et al. |
| 4,808,187 | A | 2/1989 | Patterson et al. |
| 4,955,918 | A | 9/1990 | Lee |
| 4,990,162 | A | 2/1991 | LeBlanc et al. |
| 5,413,611 | A | 5/1995 | Haslam, II et al. |
| 5,888,246 | A | 3/1999 | Gow |
| 6,344,062 | B1 | 2/2002 | Abboudi et al. |
| 7,370,896 | B2 | 5/2008 | Anderson et al. |
| 7,922,773 | B1 | 4/2011 | Kuiken |
| 8,662,552 | B2 * | 3/2014 | Torres-Jara ............ 294/111 |
| 2003/0036805 | A1 | 2/2003 | Senior |
| 2004/0078091 | A1 | 4/2004 | Elkins |
| 2005/0192677 | A1 | 9/2005 | Ragnarsdottir et al. |
| 2006/0158146 | A1 | 7/2006 | Tadano |
| 2006/0167564 | A1 | 7/2006 | Flaherty et al. |
| 2006/0212129 | A1 | 9/2006 | Lake et al. |
| 2008/0146981 | A1 | 6/2008 | Greenwald et al. |
| 2008/0262634 | A1 | 10/2008 | Puchhammer |
| 2010/0016990 | A1 * | 1/2010 | Kurtz ..................... 623/24 |
| 2010/0116078 | A1 | 5/2010 | Kim |
| 2010/0274365 | A1 | 10/2010 | Evans et al. |

FOREIGN PATENT DOCUMENTS

| | | |
|---|---|---|
| EP | 1043003 | 10/2000 |
| GB | 1585256 | 2/1981 |
| GB | 2444679 | 6/2008 |
| JP | 53-11456 | 2/1978 |
| WO | 95/24875 | 9/1995 |
| WO | 00/69375 | 11/2000 |
| WO | 03/017878 A1 | 3/2003 |
| WO | 03/017880 | 3/2003 |
| WO | 2006/069264 | 6/2006 |
| WO | 2007/063266 | 6/2007 |
| WO | 2007/076764 | 7/2007 |
| WO | 2007/076765 | 7/2007 |
| WO | 2007/127973 | 11/2007 |
| WO | 2008/044207 | 4/2008 |
| WO | 2008/098059 | 8/2008 |
| WO | 2008/098072 | 8/2008 |
| WO | 2010/018358 | 2/2010 |
| WO | 2011/001136 A2 | 1/2011 |
| WO | 2011/022569 A1 | 2/2011 |
| WO | 2011/036473 | 3/2011 |
| WO | 2011/107778 | 9/2011 |

OTHER PUBLICATIONS

International Search Report for PCT Application No. PCT/GB2012/052111; Date of Mailing Nov. 26, 2012; (5 pages).
Connolly, "Prosthetic hands from Touch Bionics," Industrial Robot: An International Journal, 35(4):290-293, 2008.
Search Report for GB Application No. GB0916895.6 dated Mar. 17, 2010, 5 pages.
Search Report for GB Application No. GB0910920.8 dated Mar. 26, 2010, 3 pages.
PCT International Search Report for PCT International Application No. PCT/GB2013/051961, mail date Dec. 11, 2013, 5 pages.
PCT International Search Report for PCT International Application No. PCT/GB2012/052021, mail date Nov. 26, 2012, 5 pages.
PCT Written Opinion of the International Searching Authority for PCT International Application No. PCT/GB2012/052021, mail date May 3, 2013, 6 pages.
PCT International Preliminary Report on Patentability for PCT International Application No. PCT/GB2010/051529, mail date Apr. 5, 2012, 7 pages.
PCT International Preliminary Report on Patentability for PCT International Application No. PCT/GB2011/050368, mail date Sep. 13, 2012, 7 pages.
PCT International Search Report and Written Opinion of International Searching Authority for PCT International Application No. PCT/GB2011/050368, mail date Jun. 21, 2011, 11 pages.
PCT International Search Report and Written Opinion of International Searching Authority for PCT International Application No. PCT/GB2010/001232, mail date Oct. 6, 2010, 9 pages.
PCT International Preliminary Report on Patentability for PCT International Application No. PCT/GB2010/001232, mail date Jan. 4, 2012, 6 pages.
PCT International Search Report and Written Opinion of International Searching Authority for PCT International Application No. PCT/GB2010/051529, mail date Jan. 4, 2011, 11 pages.

* cited by examiner

PROSTHESIS OR AN ORTHOSIS AND A METHOD FOR CONTROLLING A PROSTHESIS OR AN ORTHOSIS

CROSS REFERENCE TO RELATED APPLICATIONS

This application is a national phase under 35 U.S.C. §371 of International Application No. PCT/GB2012/052111 filed on Aug. 29, 2012, which claims priority to and benefit of GB Application No. 1116060.3 filed on Sep. 16, 2011, the entirety of these applications are incorporated by reference herein.

FIELD OF THE INVENTION

The present invention relates to a prosthesis or orthosis comprising movable components and a corresponding method for controlling movable components of a prosthesis or an orthosis.

BACKGROUND TO THE INVENTION

Prosthetic hands with motor powered digits are known. For example, WO 2007/063266 describes a prosthesis with a mechanically operable digit that is moved by an electric motor. In the prosthesis of WO 2007/063266 the electric motor is located within the digit. Shortcomings with known prostheses having motor driven digits, such as the prosthesis of WO 2007/063266 are dealt with in WO2010/149967 which provides a method of controlling a mechanically operable digit to improve the grip of the digit upon an object. The present inventor has appreciated a further need to improve known prostheses having motor driven digits, such as the prostheses of WO 2007/063266 and/or WO2010/149967.

STATEMENT OF INVENTION

The present invention has been devised in the light of the inventor's appreciation.

According to a first aspect of the present invention, there is provided a prosthesis or an orthosis comprising
 a plurality of movable components each component being movable by a respective motor; and
 a control device operative to determine when movement of at least a first component is arrested when the at least first component bears against a surface; and to move one or more further components by means of respective one or more further motors so that each subsequent component is moved upon determination that the movement of the preceding component is arrested when the preceding component bears against a surface.

Preferably, the components are digits of a hand prosthesis. The surface may, for example, be a surface of an object to be gripped between the digit and another digit, such as a thumb.

Controlling movable components of the prosthesis or orthosis to move in sequence allows the level of grip applied by a user to be varied and controlled, as opposed to known arrangements in which when a prosthetic grips something, all of the digits move and engage the object at the same time. With the control method of the present invention, the wearer can stop the process at any time, thereby controlling the level of the grip by having more or fewer digits gripping the object.

Preferably, the control device is operative to determine when movements of a first component and a second component are arrested when the first and second components bear against a surface. Preferably, one of the first and second components comprises a thumb of a hand prosthesis and the other comprises a finger, preferably, but not limited thereto, an index finger.

Preferably, the control device is operative to move the one or more further components by means of respective one or more further motors after a predetermined time interval has elapsed from the determination that the movement of the preceding component is arrested when the preceding component bears against a surface. For example, the predetermined time interval comprises 100 ms. Preferably, the one or more further components comprises a finger.

Preferably, the control device is operative to move by means of respective motors all the further components of the prosthesis or orthosis.

In one variation, the control device is operative to move by means of respective motors each subsequent component linearly, i.e. in the same order as the order in which the components are positioned on the prosthesis or orthosis. Alternatively or additionally, the control device is operative to move by means of respective motors each subsequent component non-linearly, i.e. irrespective of the order in which the components are positioned on the prosthesis or orthosis.

In one modification, the control device is operative to move the one or more further components by means of respective motors so that the sequential movement of the components occurs automatically, i.e. the sequential movement continues until a control signal to stop the sequential movement is made. Alternatively or additionally, the movement of each subsequent component is controlled by a separate control signal. Control may be by known means, such as, for example, residual digit or wrist movement, pressure sensitive resistors or signals derived from the electromyographic activity of residual muscle actions.

Preferably, the prosthesis or orthosis comprises means for providing at least one driving electrical pulse to the respective motor of some or all the components in dependence on the determination that movement of the component is arrested to thereby drive the motor so as to cause the component to bear against the surface with greater force.

Preferably, the means for providing at least one driving electrical pulse is configured to provide the at least one driving electrical pulse to the respective motor of some or all the components sequentially. Preferably, the means for providing at least one driving electrical pulse is configured to provide at least one driving electrical pulse to the respective motor of the movable components of the prosthesis or orthosis which have been caused to bear against a surface of an object. In one variation, the means for providing at least one driving electrical pulse is configured to repeat again as many times as necessary the sequential provision of the at least one driving electrical pulse to the respective motors of the relevant movable components upon completion of the sequential provision of the at least one driving electrical pulse to the respective motors of the relevant movable components.

Preferably, the means for providing at least one driving electrical pulse is configured to provide the at least one driving electrical pulse to the respective motor of some or all the components in an order which corresponds to the order in which the sequential movement of the components occurs. In one variation, the means for providing at least one driving electrical pulse is configured to provide the at least one driving electrical pulse to the respective motor linearly, i.e. in the same order as the order in which the components are positioned on the prosthesis or orthosis and, preferably, following the order of engagement of the components with an object. Alternatively or additionally, the means for providing at least one driving electrical pulse is configured to provide the at least one driving electrical pulse to the respective motor non-linearly, i.e. irrespective of the order in which the components are positioned on the prosthesis or orthosis, but, preferably, following the order of engagement of the components with an object.

Providing at least one driving electrical pulse to the respective motors causes the components (e.g. digits of the prosthesis) to bear against the surface with greater force. Thus, for example, providing at least one driving electrical pulse to the motor may cause a gripping force between the digit and the thumb to increase. The inventor has now discovered that providing at least one driving electrical pulse to the respective motors of the remaining components (e.g. fingers) further considerably increases the gripping force and, at the same time, increases the degree of flexibility of control over the grip. Providing the at least one driving electrical pulse to the respective motors in the same order as that of the sequential movement of the components further enhances the quality of the grip.

The prosthesis or orthosis of the present invention may find application in particular with arrangements in which the size and thus the motive power of the motors are constrained. More specifically, the motors may be contained in the components being moved.

Preferably, the means for providing at least one driving electrical pulse is configured to provide the at least one driving electrical pulse to the respective motor when movement of the respective component has substantially stopped. Further preferably, the control device is operative to determine when movement of the component is arrested by determining when movement of the component is substantially stopped.

Alternatively or in addition, the prosthesis or orthosis of the present invention may comprise a counter movement arrangement for arresting movement of a component in a direction opposite the direction in which the component is moved by the respective motor.

More specifically, the counter movement arrangement may comprise first and second gear components that are configured such that when they mesh with each other they present a greater resistance to movement in relation to each in one direction than in another.

More specifically, one of the first and second gear components may comprise a plurality of teeth with each tooth being asymmetric. Hence, each of the plurality of teeth may be set at an angle less than 90 degrees from a surface of the gear component from which the tooth extends.

Alternatively or in addition, the first gear component may comprise a gear wheel and the second gear component may comprise a worm. The worm may comprise a plurality of teeth that extend at an angle greater than 2 degrees from a line extending perpendicularly of the axis of rotation of the worm. More specifically, the plurality of teeth may extend at an angle of substantially 6.34 degrees to the perpendicularly extending line.

Alternatively or in addition, the component may be mechanically coupled to the respective motor by a mechanical coupling such that, in use, the component is moved by the motor by way of the mechanical coupling. More specifically, the mechanical coupling comprises at least one of a gearbox, first and second bevel gears, and a gear wheel and worm.

Alternatively or in addition, the at least one driving electrical pulse may have a positive amplitude of between substantially 3 volts and substantially 12 volts. More specifically, the driving electrical pulse may have a positive amplitude of between substantially 5 volts and substantially 9 volts. More specifically, the driving electrical pulse may have a positive amplitude of about 7 volts, such as substantially 7.2 volts.

Alternatively or in addition, the driving electrical pulses that move the component may have a positive amplitude of between substantially 3 volts and substantially 12 volts. More specifically, the driving electrical pulses that move the component may have a positive amplitude of between substantially 5 volts and substantially 9 volts. More specifically, the driving electrical pulses that move the component may have a positive amplitude of about 7 volts, such as substantially 7.2 volts.

Alternatively or in addition, the gear wheel may be attached to a support member of the prosthesis or orthosis such that the gear wheel does not rotate with respect to the support member and the worm may be in engagement with the gear wheel such that when the respective motor is operated, the component moves around the gear wheel. Alternatively or in addition, the respective motor may be coupled to a gearbox.

Alternatively or in addition, the respective motor may comprise a direct current (d.c.) motor. More specifically, motor may comprise a permanent magnet direct current (d.c.) motor.

According to a second aspect of the present invention, there is provided method of controlling movable components of a prosthesis or orthosis, the method comprising:
a) moving at least a first component by means of a motor;
determining when movement of the at least first component is arrested when the at least first component bears against a surface; and
b) moving one or more of further components by means of respective one or more further motors wherein each subsequent component is moved upon determination that the movement of the preceding component is arrested when the preceding component bears against a surface.

Determining when movement of the component is arrested may comprise measuring an electrical signal passing through the motor. For example, the measured signal may comprise an electrical current drawn by the motor.

More specifically, determining when movement of the component is arrested may comprise comparing the measured electrical signal with a threshold value. The at least one driving electrical pulse may be provided to the motor in dependence on the comparison. For example, if the measured electrical signal is current drawn by the motor the at least one driving electrical pulse may be provided to the motor when the drawn current exceeds a threshold value of current. The exceeding of a threshold value of current may indicate that movement of the component is arrested. More specifically, the threshold value may be between substantially 500 mA and 1 A. More specifically, the threshold value may be substantially 700 mA.

Alternatively or in addition, the step of determining when movement of the component is arrested may comprise determining when movement is arrested after a period during which the component is moved by the respective motor.

Alternatively or in addition, the step of providing at least one driving electrical pulse may comprise providing a plurality of driving electrical pulses.

More specifically, the plurality of driving electrical pulses may be provided to the respective motor for a predetermined period of time, e.g. selected from a range between 0.5 seconds and 1 second.

The driving electrical pulses can have a predetermined period, e.g. selected from a range between 1 second and 2 mS.

Alternatively or in addition, a driving electrical pulse may comprise a constant portion and a decaying portion, the constant portion being at substantially a same voltage over time and the decaying portion changing from the level of the constant portion to substantially zero over time.

More specifically, the constant portion may be substantially 50% of the driving electrical pulse on time and the decaying portion may be substantially 50% of the driving electrical pulse on time.

Embodiments of the second aspect of the present invention may comprise one or more features of the first aspect of the present invention and vice versa.

BRIEF DESCRIPTION OF THE DRAWINGS

The present invention will now be described by way of example only with reference to the following drawings, of which.

SPECIFIC DESCRIPTION

Figure 1:
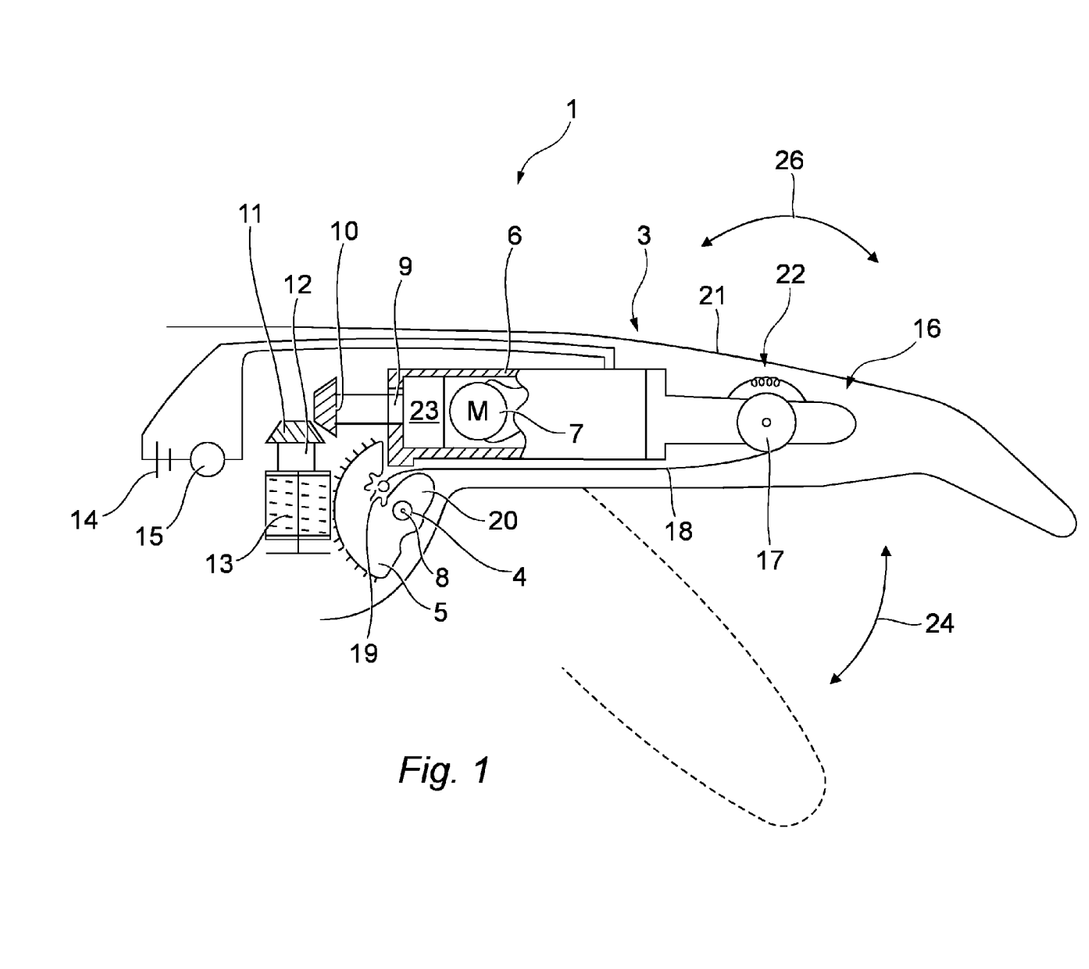
FIG. 1 is a partly cut-away view of a finger member of a prosthesis according to the present invention.

FIG. 1 shows a partly cut-away view of a hand prosthesis 1 having a finger 3 (which constitutes a component or digit). The prosthesis 1 is securely fixed in use to a patient's hand stump (not shown) in a generally known manner by means of a main body (not shown). The main body has a spindle 4 on which a gear wheel 5 is fixedly mounted. Gear wheel 5 is of roughly semi-circular profile. Finger 3 extends generally tangentially with respect to the gear wheel 5. Finger 3 has a generally tubular housing 6, in which is mounted a motor 7 having a gearbox system 23. The gearbox system 23 provides for different torque—output drive speed ratios to be selected from a range of different ratios. A GP 10 A Ø10 mm, 0.01 to 0.15 Nm planetary gearhead (order no. 218417) from Maxon Motor UK Limited, Maxon House, Hogwood Lane, Finchampstead, Berkshire RG40 4QW, UK is used in one form; this gearhead has a reduction ratio of 64:1. Lugs (not shown) depend from the underside of the tubular housing 6 and are rotatably mounted on the spindle to allow for rotation of the finger 3 in relation to the spindle 4 and gear wheel 5. The centre 8 of the spindle 4 defines an axis (which constitutes a gear wheel axis) about which the finger 3 rotates. The housing 6 containing the motor 7 corresponds to the proximal phalanx of a finger and the joint formed between the spindle 4 and the lugs depending from the housing 6 correspond to the metacarpophalangeal (MCP) or knuckle joint of a finger.

A drive shaft 9 extends from the motor 7 and gearbox system 23. A first bevel gear 10 is mounted on the distal end of the drive shaft 9. A second bevel gear 11 is mounted within the prosthesis 1 such that an axis of rotation of the second bevel gear 11 is at substantially 90 degrees to an axis of rotation of the first bevel gear 10. The gear ratio of the first and second bevel gears 10, 11 is substantially 1 to 1, although the gear ratio can be readily changed by known means. The second bevel gear 12 is mounted on the same shaft 12 as a worm 13. The worm 13 is located such that it engages with a toothed, curved peripheral edge of gear wheel 5. As can be seen from FIG. 1 the worm 13 extends laterally to the housing 6 at an angle of about 90 degrees. The worm and gear wheel have a 25:1 reduction ratio.

It should be noted that the worm 13 is located in the prosthesis such that it is outside the housing 6. Thus, the worm is located within the hand of the prosthesis and not the finger 3 even though the prosthesis is structured such that the worm 13 moves with the housing 6 upon operation of the finger 3, as described below.

The motor 7 is a permanent magnet DC motor having a substantially linear relation between torque and drive current. A Maxon RE 10 Ø10 mm, precious metal brushes, 1.5 Watt motor (order no. 118392, 118394 or 118396) from Maxon Motor UK Limited, Maxon House, Hogwood Lane, Finchampstead, Berkshire RG40 4QW, UK is used where a physically larger and more powerful motor is required. A Maxon RE 10 Ø10 mm, precious metal brushes, 0.75 Watt motor (order no. 118383, 118385 or 118386) from Maxon Motor UK Limited is used where a physically smaller and less powerful motor is required. In normal use the motor rotates at 21,000 rpm. The motor is powered by small rechargeable batteries 14, which may be mounted remotely of the prosthesis. The motor is controlled by means of switches 15, which are actuated by known means, e.g. residual digit movement or wrist movement. Alternatively or in addition, control may be by means of pressure sensitive resistors or signals derived from the electromyographic activity of residual muscle actions. In forms of the invention in which the prosthesis comprises a plurality of other digits, i.e. a thumb and one or more other fingers, control by known means provides for independence of movement of the digits or groups of digits. In the case of a finger or a thumb the motor 7 has low speed, high torque characteristics.

Finger 3 has a finger tip portion 16 corresponding to the middle and distal phalanges of a finger (and which constitutes a second digit member), which forms with the distal end of the housing 6 a proximal joint 17 corresponding to a proximal intermediate phalangeal (PIP) joint of a finger. Arrow 24 represents movement of the finger 3 about axis 8 (i.e. the MCP joint) and arrow 26 represents movement of finger tip portion 16 about PIP joint 17. An inextensible belt or chord 18 is attached at a first end to the gear wheel 5 in an aperture 19 provided in the gear wheel 5, passes over a protrusion 20 formed on the gear wheel and is attached at a second end to the finger tip portion 16. A helical spring 22 is connected at one end to the end of housing 6 and at a second opposing end to the finger tip portion 16. The prosthesis is clad in a known manner with an overlay 21 of silicone rubber or the like to provide an aesthetically acceptable appearance which is as similar as practicable to a normal hand.

A similar motor arrangement as that shown in FIG. 1 is provided for movement of each digit of the prosthesis of the invention.

The hand prosthesis 1 further comprises a circuit board (not shown) containing electronic circuitry (which constitutes a control device), which is operative to control operation of the motor as described in detail below. The electronic circuitry comprises a TMS320F2808ZGMA, which is a 32-bit digital signal controller from Texas Instruments, and a flash memory IC. The design of circuitry based on and around the digital signal controller and the flash memory will be readily within the grasp of the ordinary design capabilities of the skilled person. The control processes described below are embodied in firmware, which is stored in and executed on the digital signal controller and the flash memory IC. The electronic circuitry also comprises an H-bridge, which is used to provide for bi-directional drive of the motor, and a current measurement circuit, such as a MAX4073 from Maxim Integrated Products, which is configured to measure current drawn through the H-bridge. The H-bridge will be well known to the skilled person and the design of circuitry based on the H-bridge and the current measurement circuit will be readily within the grasp of the ordinary design capabilities of the skilled person.

In use the wearer actuates the finger by one of the means described above, e.g. by way of electromyographic activity of residual muscle actions. Operation of the motor 7 in response to actuation causes rotation of the first bevel gear 10, which rotates the second bevel gear 11 together with the worm 13. As the worm 13 rotates it progresses around the peripheral surface of the fixed gear wheel 5 either clockwise or anti-clockwise depending on the direction of rotation of the motor 7. This moves the finger 3 about the axis 8 in the direction indicated by arrow 24. As finger 3 moves about axis 8 in a downward direction the distance between the point of attachment of the belt 18 in aperture 19 of the worm gear wheel 5 and the proximal joint 17 reduces. This is because aperture 19 is offset from the axis of the gear wheel as shown in FIG. 1. As the distance reduces the fixed length belt 18 pulls on the finger tip portion 16 against the bias of the helical spring 22 to rotate the finger tip portion 16 clockwise in relation to the rest of the finger 3. Upon reversal of the direction of rotation of the finger 3 about the axis, i.e. movement of finger 3 upwards, tension is released on the belt 18 and the spring 22 exerts a bias on the finger tip portion 16 to return the finger tip portion to the extended position shown in FIG. 1.

Figure 3:
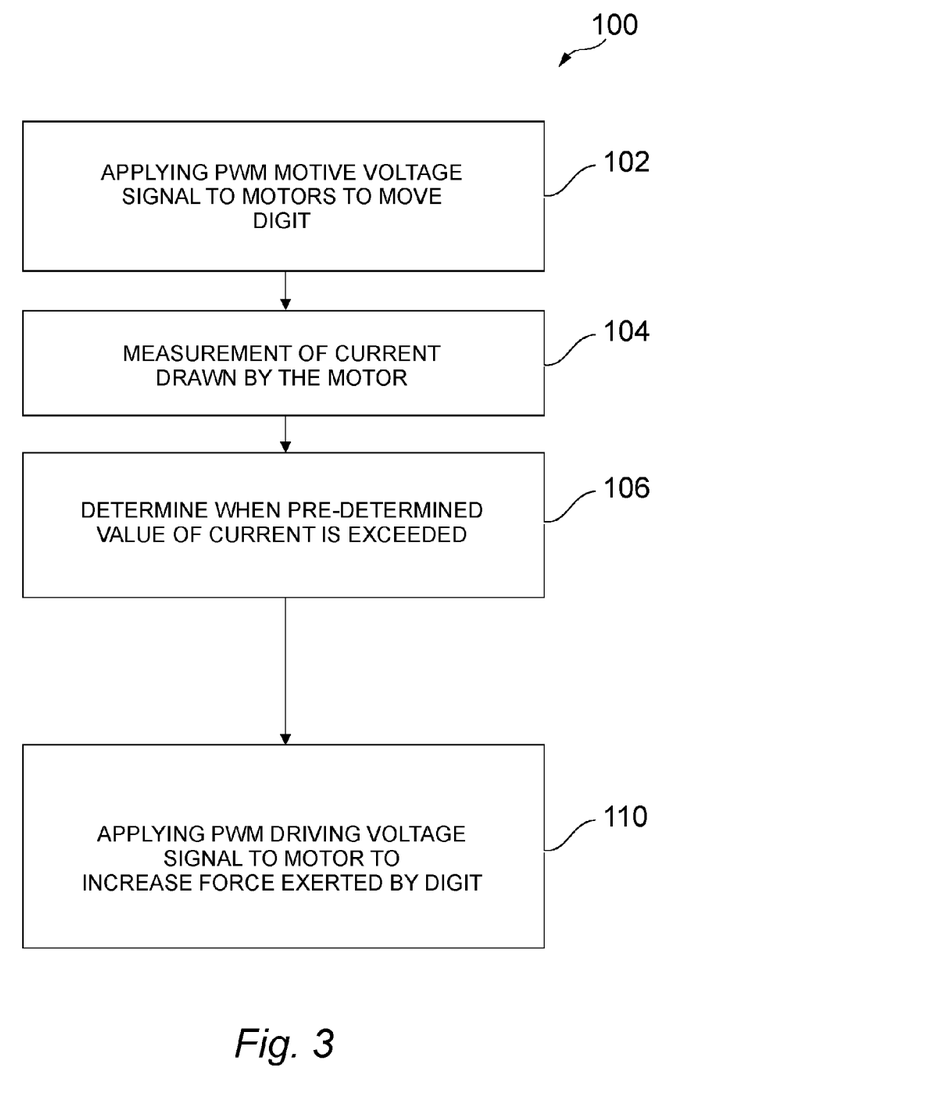
FIG. 3 is a flow chart representation of the procedural steps of applying electric pulses to a motor performed by the prosthesis.

Further operation of the prosthesis will now be described with reference to FIG. 3, which is a flow chart representation 100 of procedural steps performed by the prosthesis. Movement of the finger 3 (which constitutes a component of a prosthesis or orthosis) by means of the motor 7 in a first direction may, depending on how the prosthesis is being used, cause the finger tip portion 16 to bear against a surface, such as a surface of an object to be held between the finger 7 and a prosthetic thumb. Movement of the finger is achieved by the application of a pulse width modulated (PWM) motive voltage signal to the motor 102 (which constitutes a plurality of spaced apart electrical motive pulses). The mark to space ratio of the PWM motive voltage signal is varied depending on the level of electrical power that is required to be delivered to the motor. The PWM motive voltage signal has a frequency of 41.6 kHz. As the finger tip portion 16 grips the object (which constitutes bearing against a surface), movement of the finger is arrested. As finger movement is arrested, there is a progressive increase in the current drawn by the motor 7 through the H-bridge. The progressive increase in the current drawn by the motor 7 is shown in FIG. 3, which shows the level of current drawn by the motor over time. The current drawn by the motor 7 is measured by the current measurement circuit 104 and compared with a predetermined value of current stored in the digital signal controller. As can be seen from FIG. 3 the predetermined level of current is substantially 700 mA. When the predetermined value of current is exceeded 106, the digital signal controller commences a 500 mS delay. After the 500 mS delay, a pulse width modulated (PWM) driving voltage signal (which constitutes a plurality of driving electrical pulses) is applied 110 to the motor 7. In another form, no 500 mS delay is applied and the pulse width modulated (PWM) driving voltage signal is applied when the predetermined value of current is exceeded. Selection between applying the delay and not applying the delay is made by the user depending on his or her preference or requirements. Selection by the user is by way of a Graphical User Interface (GUI) on a Personal Computer (PC), the prosthesis or orthosis having a communications port that provides for communication of configuration data with the PC. The design of necessary communications hardware and firmware and the design of a PC resident GUI will be readily within the grasp of the ordinary design capabilities of the skilled person.

The inventor has found that application of the PWM driving voltage signal to the motor increases the force exerted by the finger beyond the level achievable by application of the PWM motive voltage signal alone. The greater duration of pulse application, i.e. the larger number of pulses applied, progressively increases the force applied by the finger. For example, application of the PWM driving voltage signal for 3 seconds causes the finger to exert a force of substantially 3.5 kg whereas application of the PWM motive voltage signal alone achieves a force of 1 kg.

Counter movement of the finger before, during and after the application of the PWM driving voltage signal is resisted by the configuration of the gear wheel and the worm. More specifically, the teeth of the worm extend at an angle of substantially 6.34 degrees from a line extending perpendicularly of the axis of rotation of the worm. When the teeth of the gear wheel and the worm mesh with each other, the angle of the teeth of the worm provides for a greater resistance to movement of the finger in a direction opposing the direction in which the finger exerts its force than in the direction in which the finger exerts its force.

Figure 2:
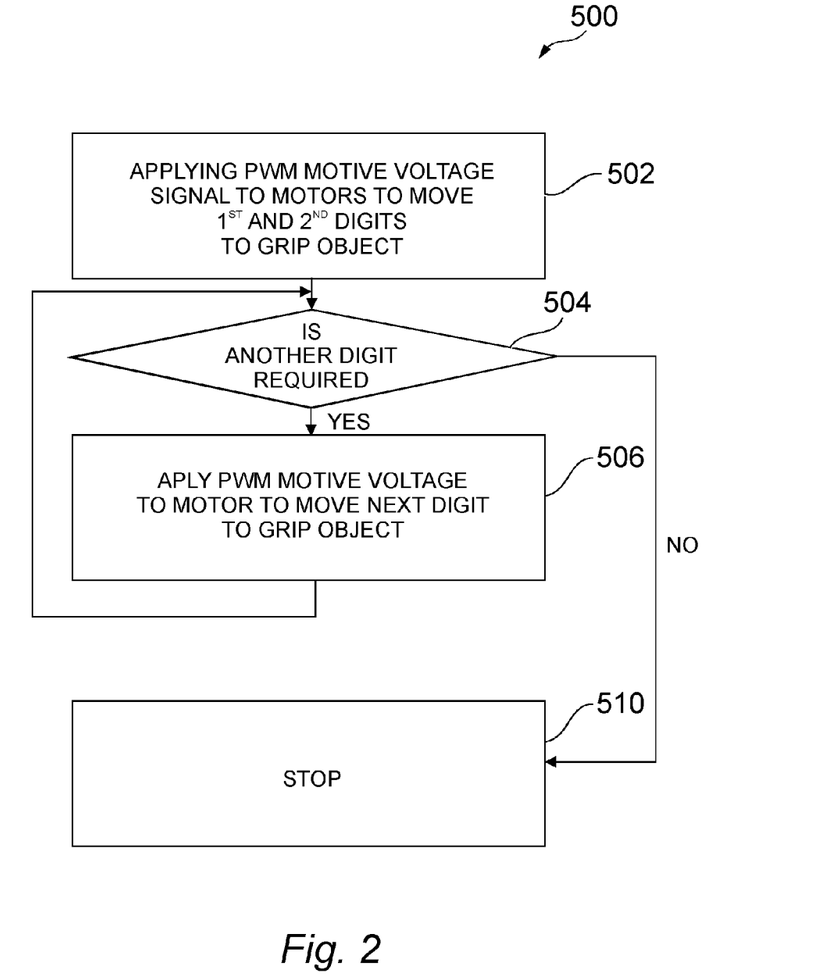
FIG. 2 is a flow chart representation of the procedural steps of moving digits performed by the prosthesis.

The method of controlling the digits of a prosthesis or orthosis according to the invention will be described with reference to FIG. 2 which is a flow chart representation 500 of procedural steps performed by the prosthesis. Initially, as at 502, respective motors move two opposing digits, normally, a thumb and an index finger, to grip an object. When it has been determined that movement of the first two digits is arrested, i.e. when the two digits bear against a surface, the user makes a judgement whether a further digit is required for gripping, as at 504. If so, one or more of further digits are then moved, as at 506, in sequence by means of respective further motors. In the present invention, each subsequent digit is moved only when it has been determined that the movement of the preceding digit is arrested, i.e. when the preceding component bears against a surface.

If no further digits are required, as at 510, the wearer can stop the process at any time so that only some and not all of the digits grip the object in addition to the first two. This enables the user to control the level of the grip by having more or fewer digits gripping the object. Preferably, the method of the invention involves moving all the digits of the prosthesis or orthosis to grip an object.

A subsequent digit is moved after a predetermined time interval has elapsed from the determination that the movement of the preceding digit is arrested when the preceding digit bears against a surface. For example, the predetermined time interval comprises 100 mS.

In one variation, the control circuitry controls the digits to move linearly in sequence, i.e. in the same order as the order in which the digits are positioned on the prosthesis or orthosis. Alternatively or additionally, the control circuitry can be adapted to control the digits to move non-linearly in sequence, i.e. irrespective of the order in which the components are positioned on the prosthesis or orthosis, e.g. to move middle finger first, then little finger, then ring finger.

The control circuitry can be adapted to control the sequential movement of the digits so that the digits move in sequence automatically, i.e. so that the sequential movement continues until a control signal to stop the sequential movement is made. Alternatively or additionally, control circuitry can be adapted so that a separate control signal is required to control the movement of each subsequent digit.

As discussed above, control may be by known means, such as, for example, residual digit or wrist movement, pressure sensitive resistors or signals derived from the electromyographic activity of residual muscle actions.

The method of controlling the digits of a prosthesis or orthosis according to the invention also includes providing at least one driving electrical pulse, such as described with reference to FIG. 3, to the respective motor of some or all the digits sequentially upon the determination that movement of the digit is arrested to thereby drive the motor so as to cause the digit to bear against the surface with greater force. Preferably, the at least one driving electrical pulse is provided to the respective motor of all the movable components of the prosthesis or orthosis which have been caused to bear against a surface of an object by the respective motor. Upon completion of the sequence of providing of the at least one driving electrical pulse to the respective motors of the relevant movable components, the sequence of providing the at least one driving electrical pulse is repeated again as many times as necessary. In use, preferably, the sequence of driving pulses is repeated as long as the object is being gripped.

The driving electrical pulse is provided to the respective motors of the digits in an order which corresponds to the order in which the sequential movement of the digits occurs during gripping, i.e. the driving electrical pulse can be provided to the respective motor linearly i.e. in the same order as the order in which the digits are positioned on the prosthesis or orthosis, or non-linearly, irrespective of the order in which the digits are positioned on the prosthesis or orthosis, but in any case following the order of gripping of the digits with an object.

Providing at least one driving electrical pulse to the motors of the first two fingers, e.g. index finger and thumb, causes the digits of the prosthesis to bear against the object surface with greater force. Providing at least one driving electrical pulse to the respective motors of the remaining digits further considerably increases the gripping force and, at the same time, increases the degree of flexibility of control over the grip.

The procedural steps described above are embodied in firmware, which is resident in and executed on the digital signal controller. The creation of such firmware is within the ordinary design capabilities of the skilled person.

It will be appreciated that variations are possible within the scope of the invention as defined in the appended claims.

The invention claimed is:

1. A prosthesis or an orthosis comprising:
   a plurality of movable components each component being movable by a respective motor;
   a current measurement circuit which measures the current drawn by the respective motors; and
   a control device which controls movement of the movable components and stores predetermined current values for the respective motors;
   wherein the control device compares the current measured by the current measurement circuit with the predetermined current value stored for a first motor so as to determine when movement of at least a first component moveable by the first motor is arrested when the at least first component bears against a surface; and the control device moves one or more further components by means of respective one or more further motors so that each subsequent component is moved upon determination that the movement of the preceding component is arrested when the preceding component bears against a surface.

2. A prosthesis or an orthosis as claimed in claim 1 wherein the control device compares the current measured by the current measurement circuit with the predetermined current value stored for first and second motors so as to determine when movements of a first component and a second component are arrested when the first and second components bear against a surface.

3. A prosthesis or an orthosis as claimed in claim 2 wherein one of the first and second components comprises a thumb of a hand prosthesis and the other comprises a finger.

4. A prosthesis or an orthosis as claimed in claim 3, wherein the other component comprises an index finger.

5. A prosthesis or an orthosis as claimed in claim 1 wherein the control device moves the one or more further components by means of respective one or more further motors after a predetermined time interval has elapsed from the determination that the movement of the preceding component is arrested when the preceding component bears against a surface.

6. A prosthesis or an orthosis as claimed in claim 5, wherein the predetermined time interval comprises 100 ms.

7. A prosthesis or an orthosis as claimed in claim 5 wherein the one or more further components comprises a finger.

8. A prosthesis or an orthosis as claimed claim 1, wherein the control device is operative to move by means of respective motors all the further components of the prosthesis or orthosis.

9. A prosthesis or an orthosis as claimed claim 1, wherein the control device moves by means of respective motors each subsequent component linearly, in the same order as the order in which the components are positioned on the prosthesis or orthosis.

10. A prosthesis or an orthosis as claimed in claim 1, wherein the control device moves by means of respective motors each subsequent component non-linearly, irrespective of the order in which the components are positioned on the prosthesis or orthosis.

11. A prosthesis or an orthosis as claimed in claim 1, wherein the control device moves the one or more further components by means of respective motors so that the sequential movement of the components occurs automatically, such that the sequential movement continues until a control signal to stop the sequential movement is made.

12. A prosthesis or an orthosis as claimed in claim 1, wherein the movement of each subsequent component is controlled by a separate control signal.

13. A prosthesis or an orthosis as claimed in claim 1, wherein the prosthesis or orthosis comprises means for providing at least one driving electrical pulse to the respective motor of some or all the components in dependence on the determination that movement of the component is arrested to thereby drive the motor so as to cause the component to bear against the surface with greater force.

14. A prosthesis or an orthosis as claimed in claim 13, wherein the means for providing at least one driving electrical pulse is configured to provide the at least one driving electrical pulse to the respective motor of some or all the components sequentially.

15. A prosthesis or an orthosis as claimed in claim 13, wherein the means for providing at least one driving electrical pulse is configured to provide at least one driving electrical pulse to the respective motor of the movable components of the prosthesis or orthosis which have been caused to bear against a surface of an object.

16. A prosthesis or an orthosis as claimed in claim 14, wherein the means for providing at least one driving electrical pulse is configured to repeat again as many times as necessary the sequential provision of the at least one driving electrical pulse to the respective motors of the relevant movable components upon completion of the sequential provision of the at least one driving electrical pulse to the respective motors of the relevant movable components.

17. A prosthesis or an orthosis as claimed in claim 13, wherein the means for providing at least one driving electrical pulse is configured to provide the at least one driving electrical pulse to the respective motor of some or all the components in an order which corresponds to the order in which the sequential movement of the components occurs.

18. A prosthesis or an orthosis as claimed in claim 13, wherein the means for providing at least one driving electrical pulse is configured to provide the at least one driving electrical pulse to the respective motor linearly, in the same order as the order in which the components are positioned on the prosthesis or orthosis.

19. A prosthesis or an orthosis as claimed in claim 13, wherein the means for providing at least one driving electrical pulse is configured to provide the at least one driving electrical pulse to the respective motor linearly, in the same order as the order in which the components are positioned on the prosthesis or orthosis and following the order of engagement of the components with an object.

20. A prosthesis or an orthosis as claimed in claim 13, wherein the means for providing at least one driving electrical pulse is configured to provide the at least one driving electrical pulse to the respective motor non-linearly, irrespective of the order in which the components are positioned on the prosthesis or orthosis.

21. A prosthesis or an orthosis as claimed in claim 13, wherein the means for providing at least one driving electrical pulse is configured to provide the at least one driving electrical pulse to the respective motor non-linearly, irrespective of the order in which the components are positioned on the prosthesis or orthosis, but following the order of engagement of the components with an object.

22. A prosthesis or an orthosis as claimed in claim 13, wherein the means for providing at least one driving electrical pulse is configured to provide the at least one driving electrical pulse to the respective motor when movement of the respective component has substantially stopped.

23. A prosthesis or an orthosis as claimed in claim 22, wherein the control device is operative to determine when movement of the component is arrested by determining when movement of the component is substantially stopped.

24. A prosthesis or an orthosis as claimed in claim 1, wherein the components are digits of a hand prosthesis.

25. A prosthesis or an orthosis as claimed in claim 24, wherein the surface is a surface of an object to be gripped between the digit and another digit.

26. A method of controlling movable components of a prosthesis or orthosis, the method comprising:
   a) moving at least a first component by means of a first motor;
   b) measuring the current drawn by the first motor;
   c) comparing the current drawn by the first motor with a stored current value so as to determine when movement of the at least first component is arrested when the at least first component bears against a surface; and
   d) moving one or more further components by means of respective one or more further motors wherein each subsequent component is moved upon determination that the movement of the preceding component is arrested when the preceding component bears against a surface.

27. A method as claimed in claim 26, wherein the step a) comprises moving a first component and a second opposing component by means of respective motors and determining when movements of the first and second component are arrested when the first and second components bear against a surface.

28. A method as claimed in claim 26, wherein the step d) comprises moving the one or more further components after a predetermined time interval has elapsed from the determination that the movement of the preceding component is arrested when the preceding component bears against a surface.

29. A method as claimed in claim 28, wherein the predetermined time interval comprises 100 ms.

30. A method as claimed in claim 26, wherein the step d) comprises moving all the further components of the prosthesis or orthosis.

31. A method as claimed in claim 26, wherein the step d) comprises moving each subsequent component linearly, in the same order as the order in which the components are positioned on the prosthesis or orthosis.

32. A method as claimed in claim 26, wherein the step d) comprises moving each subsequent component non-linearly, irrespective of the order in which the components are positioned on the prosthesis or orthosis.

33. A method as claimed in claim 26, wherein the sequential movement of the components in the step d) occurs automatically, wherein the sequential movement continues until a control signal to stop the sequential movement is made.

34. A method as claimed in claim 26, wherein the movement of each subsequent component is controlled by a separate control signal.

35. A method as claimed in claim 26, wherein the method further comprises the step of
   e) providing at least one driving electrical pulse to the respective motor of some or all the components in dependence on the determination that movement of the component is arrested to thereby drive the motor so as to cause the component to bear against the surface with greater force.

36. A method as claimed in claim 35, wherein the step e) includes providing the at least one driving electrical pulse to the respective motor of some or all the components sequentially.

37. A method as claimed in claim 35, wherein the step e) comprises providing at least one driving electrical pulse to the respective motor of the movable components of the prosthesis or orthosis which have been caused to bear against a surface of an object.

38. A method as claimed in claim 37, wherein upon completion of the sequential provision of the at least one driving electrical pulse to the respective motors of the relevant movable components, the step e) is repeated again as many times as necessary.

39. A method as claimed in claim 35, wherein the step e) includes providing the at least one driving electrical pulse to the respective motor of some or all the components in an order which corresponds to the order in which the sequential movement of the components occurs in the step d).

40. A method as claimed in claim 35, wherein the at least one driving electrical pulse is provided to the respective motor linearly in the same order as the order in which the components are positioned on the prosthesis or orthosis.

41. A method as claimed in claim 35, wherein the at least one driving electrical pulse is provided to the respective motor linearly in the same order as the order in which the components are positioned on the prosthesis or orthosis and following the order of engagement of the components with an object.

42. A method as claimed in claim 35, wherein the at least one driving electrical pulse is provided to the respective motor non-linearly, irrespective of the order in which the components are positioned on the prosthesis or orthosis.

43. A method as claimed in claim 35, wherein the at least one driving electrical pulse is provided to the respective motor non-linearly, irrespective of the order in which the components are positioned on the prosthesis or orthosis, but following the order of engagement of the components with an object.

44. A method as claimed in claim 35, wherein the at least one driving electrical pulse is provided to the motor when movement of the respective component has substantially stopped.

45. A method as claimed in claim 44, wherein the step of determining when movement of the component is arrested comprises determining when movement of the component is substantially stopped.

46. A method as claimed in claim 26, wherein the components are digits of a hand prosthesis.

\* \* \* \* \*